United States Patent [19]

Anderson et al.

[11] 4,284,562
[45] Aug. 18, 1981

[54] PROCESS FOR PREPARING PYRROLE-2-ACETIC ACIDS

[75] Inventors: Neal G. Anderson, North Brunswick, N.J.; John R. Carson, Norristown, Pa.

[73] Assignee: McNeilab, Inc., Fort Washington, Pa.

[21] Appl. No.: 161,240

[22] Filed: Jun. 20, 1980

Related U.S. Application Data

[63] Continuation-in-part of Ser. No. 97,757, Nov. 27, 1979, abandoned.

[51] Int. Cl.$^3$ .......................................... C07D 207/337
[52] U.S. Cl. .................................................. 260/326.2
[58] Field of Search ...................................... 260/326.2

[56] References Cited

U.S. PATENT DOCUMENTS

| 3,752,826 | 8/1973 | Carson | 260/326.47 |
| 3,957,818 | 5/1976 | Carson | 260/326.2 |
| 3,998,844 | 12/1976 | Carson | 260/326.47 |
| 4,207,237 | 6/1980 | Carson et al. | 260/326.2 |
| 4,216,150 | 8/1980 | Carson et al. | 260/326.2 |

FOREIGN PATENT DOCUMENTS 1541594 8/1968 France ................................ 260/326.2

OTHER PUBLICATIONS

Blinn et al., J. Am. Chem. Soc., vol. 76, pp. 37–39, (1954).

*Primary Examiner*—Alton D. Rollins

[57] ABSTRACT

N-H and N-loweralkyl pyrrole-2-acetic acids are prepared by the reduction of 1-H and 1-loweralkyl-α-trichloromethylpyrrole-2-methanol with sodium dithionite (sodium hydrosulfite) in the presence of a base, MOH, wherein M is an alkali metal, an alkaline earth metal or tetraalkyl ammonium.

6 Claims, No Drawings

PROCESS FOR PREPARING PYRROLE-2-ACETIC ACIDS

This application is a continuation-in-part of copending application Ser. No. 97,757, filed Nov. 27, 1979, abandoned.

This invention relates to a novel process for making N-H and N-loweralkyl pyrrole-2-acetic acids (II) from 1-H and 1-loweralkyl-α-trichloromethylpyrrole-2-methanols (I) respectively, which reaction may be illustrated by the following schematic diagram:

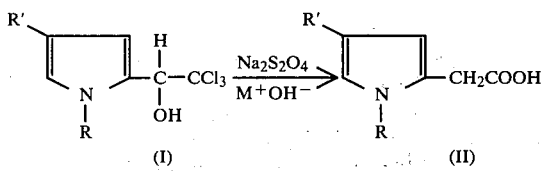

wherein: R represents a member selected from the group consisting of hydrogen and loweralkyl, and R' is hydrogen or loweralkyl, preferably methyl.

The reaction is carried out in the presence of (a) sodium dithionite ($Na_2S_2O_4$), which is also called sodium hydrosulfite and which acts as a reducing agent; and (b) a base of the formula MOH, wherein M represents a member selected from the group consisting of alkali metal, alkaline earth metal and tetraalkylammonium.

As used herein, "loweralkyl" may be straight- or branch-chained hydrocarbons having from 1 to 6 carbon atoms, such as, for example, methyl, ethyl, propyl, butyl, isobutyl, pentyl and hexyl.

Examples of MOH as alkali metal hydroxides include KOH, NaOH and LiOH; as alkaline earth hydroxides include $Ca(OH)_2$; and as tetraalkylammonium hydroxides include $C_1$–$C_6$ alkyls such as tetramethyl ammonium hydroxide and tetrabutylammonium hydroxide.

The above acids (II) are useful as intermediates in the manufacture of tolmetin, 1-methyl-5-(4-methylbenzoyl)pyrrole-2-acetic acid and compounds closely related thereto wherein the N atom of the pyrrole is unsubstituted or else substituted with other lower alkyl groups. Tolmetin and the aforesaid compounds closely related thereto are useful as non-steroidal anti-inflammatory agents for the treatment of rheumatoid arthritis. Tolmetin is commercially available as the sodium salt dihydrate (TOLECTIN* Tolmetin Sodium). Tolmetin and the aforesaid compounds closely related thereto, and a process for their manufacture is disclosed in Carson, U.S. Pat. No. 3,752,826.

*Trademark of Johnson & Johnson or Subsidiary.

The acids (II) made by the process of the present invention are converted to the above known, useful compounds by means of known procedures. Thus, the acids (II) are esterified to the lower alkyl esters thereof as taught in French Pat. No. 1,541,594, and the esters are then converted to tolmetin or the above-discussed compounds closely related thereto as taught in U.S. Pat. No. 3,752,826 (for the compounds wherein the N atom of the pyrrole is unsubstituted) and in U.S. Pat. No. 3,998,844 (for the compounds wherein the N atom of the pyrrole is lower alkyl substituted).

The various trichloromethylpyrrole-2-methanol starting materials (I) used in the process of the present invention are either known compounds, disclosed in R. C. Blinn, F. A. Gunther, and R. L. Metcalf, J. Am. Chem. Soc., 76, 37 (1954), i.e., (I), R=H and $R_2$=$CH_3$, or can be made by following the procedure taught in that publication except utilizing the particular N-loweralkylpyrrole in place of N-methylpyrrole needed to obtain the desired specific N-loweralkyl-α-trichloromethylpyrrole-2-methanol compound.

In carrying out the process of the present invention, the reaction conditions can be widely varied. While a single molar equivalent of $Na_2S_2O_4$ (sodium dithionite) can be used, much better yields are obtained by using an excess of $Na_2S_2O_4$. A total of four molar equivalents of the MOH base are consumed in the reaction and enhanced yields are obtained by employing a quantity of base in excess of this amount. The reaction can be conducted over a wide range of temperatures, from 0°–100° C. with 20°–80° C. being the preferred range.

The following examples are intended to illustrate, but not to limit, the scope of the present invention.

Examples I, IA, IB, IC, ID, and IE are all related. Example I teaches the general conditions which can be used to carry out the process of the present invention, using the compounds (I) and (II) wherein R is methyl and R' is hydrogen to exemplify the reaction. Examples I(A)–I(E) illustrate the effect on the yields obtained when the reaction amounts and conditions used in Example I are varied.

The effect on the yield of varying the relative amounts of sodium dithionite [Example I(A)], of varying the relative amounts of the MOH base [Example I(B)], of varying the time of addition of the MOH base [Example I(C)], of varying the particular cation of the MOH base [Example I(D)] and of varying the reaction temperature [Example I(E)] are all shown.

Example II teaches preferred conditions for carrying out the process of the present invention where R is loweralkyl having up to 6 carbon atoms and R' is hydrogen using the compounds (I) and (II) where R is methyl to exemplify the reaction.

Example III teaches the process of the present invention using the compounds (I) and (II) where R and R' each are H to exemplify the reaction.

Example IV teaches the process of the present invention using the compounds (I) and (II) where R=$CH_3$ and R'=H to exemplify the reaction, and then shows making the methyl ester thereof.

Example V and VI teach the process of the present invention using the compounds (I) and (II) where R and R' are each methyl to exemplify the reaction, and then Example VII shows making the ethyl ester thereof. Example VIII teaches making the starting material (I) for Examples V and VI.

EXAMPLE I

1-Methyl-pyrrole-2-acetic acid

This example follows the reaction illustrated in the schematic diagram wherein R is methyl in (I) and (II).

General Conditions

A 50 ml. round-bottomed flask is charged with a suspension of sodium dithionite ($Na_2S_2O_4$) (sodium hydrosulfite) (0.66 to 4.59 g; 3.77 mmol to 26.39 mmol; 1 to 7 molar equivalents) (commercial, used without purification or analysis) in 6 ml $H_2O$+0.5 ml methanol, and to this is added 0.86 g (3.77 mmol) 1-methyl-α-trichloromethyl-pyrrole-2-methanol. An oil bath, preheated to 55°±3° C., is applied, and with magnetic stirring, there is added a solution of 4–7 molar equivalents of the hydroxide (MOH) in 8 ml H$_2$O over the period of 1 min. to 0.5 hours. After 1.5 hours, total reaction time, the flask is cooled. Following washing of the aqueous phase with 10–15 ml ethyl ether (Et$_2$O), it is acidified with HCl and solid NaCl is added. The aqueous phase is extracted three times with 30 ml of Et$_2$O. The latter organic phases are combined and dried over Na$_2$SO$_4$. The solvent is removed by rotary evaporator to give a brownish-yellow solid. This material is identified by NMR and TLC as being 1-methylpyrrole-2-acetic acid. The yields are quoted without further purification.

EXAMPLE IA

Varying Equivalents of Na$_2$S$_2$O$_4$ Used

Following the general conditions of Example I, using 6 molar equivalents of KOH (pellets, 85%; 1.49 g, 22.6 mmol) with the addition time of the basic solution being 1.5 minutes, there can be obtained the following yields as a function of equivalents of Na$_2$S$_2$O$_4$ employed:

| Equiv. Na$_2$S$_2$O$_4$ | Yield (%) | Yield (g) |
|---|---|---|
| 1 | 32 | 0.17 |
| 2 | 55 | 0.29 |
| 3 | 61 | 0.32 |
| 4 | 69 | 0.36 |
| 5 | 67 | 0.35 |
| 6 | 63 | 0.33 |
| 7 | 63 | 0.33 |

EXAMPLE IB

Varying Amount of Base Used

Following the general conditions of Example I, using 2.28 g Na$_2$S$_2$O$_4$ (3.47 eq, 13.1 mmol) with the basic solution added over 1.5 min., there can be obtained the following yields as a function of equivalents KOH used:

| Equivalents KOH | Yield (g) | Yield % |
|---|---|---|
| 4 | 0.29 | 55 |
| 5 | 0.31 | 60 |
| 6* | 0.41 | 78 |
| 7 | 0.34 | 64 |

EXAMPLE IC

Varying Time of Addition of Basic Solution

Following the general conditions of Example I, using 2.28 g of Na$_2$S$_2$O$_4$ (13.1 mmol, 3.47 eq) and 1.49 g of KOH (85% pellets; 22.6 mmol, 6 eq), there can be obtained the following yields as a function of the time of addition:

| Time | Yield (g) | Yield (%) |
|---|---|---|
| 65 sec. | 0.31 | 59 |
| 15 min. | 0.35 | 67 |
| 30 min. | 0.30 | 57 |

EXAMPLE ID

Varying the Cation of Basic Solution

Following the general conditions of Example I, but using 2.28 g of Na$_2$S$_2$O$_4$ (13.1 mmol, 3.47 eq), 22.6 mmol of base used, in 8 ml H$_2$O (6 eq) time of addition: 1.5 min., there can be obtained the following yields:

| Base | Yield (g) | Yield (%) |
|---|---|---|
| NaOH | 0.29 | 55 |
| *ME$_4$NOH | 0.32 | 61 |
| **KOH | 0.41 | 78 |

*Base dissolved in 20.6 ml H$_2$O (stock solution) from Aldrich)
**Time of addition: 5 min.

EXAMPLE IE

Varying the Temperature

A 50 ml round-bottomed flask, fitted with a magnetic stirrer and addition funnel, is charged with a suspension of 2.28 g (13.1 mmol, 3.47 equiv.) of sodium hydrosulfite+0.86 g (3.77 mmol) 1-methyl-α-trichloromethyl-pyrrole-2-methanol in 4 ml H$_2$O+0.5 ml CH$_3$OH. An ice bath or preheated oil bath is then applied (unless the reaction is run at ambient temperature). Over 2 min., a solution of 1.49 g. of potassium hydroxide pellets (22.6 mmol, 6 equiv.) in 8 ml H$_2$O is added dropwise. The reaction is worked up after 1.5 hr by extracting with 10 ml Et$_2$O, and the aqueous phase is acidified with concentrated HCl to pH 1–2, and then saturated with solid NaCl. The suspension is extracted 3× with 30 ml. portions of Et$_2$O, and the combined organic phases were dried over Na$_2$SO$_4$. The yields of N-methylpyrrole-2-acetic acid are:

| Temperature | Weight Product | Yield |
|---|---|---|
| 0° C. | 0.14 | 27% |
| 24° C. | 0.30 | 57% |
| 55° C. | 0.41 | 78% |
| 76° C. | 0.26 | 50% |
| 100° C. | 0.08 | 15% |

EXAMPLE II

1-Methyl-pyrrole-2-acetic acid

A solution of 1.49 g (85%, 22.6 mmol, 6 eq) potassium hydroxide in 8 ml H$_2$O is prepared.

A 50 ml round-bottomed flask, fitted with magnetic stirrer, oil bath preheated to 56° C. and addition funnel, is charged with a solution of 2.28 g (13.1 mmol, 3.47 eq) sodium hydroxulfite in 6 ml H$_2$O+2 ml of the above KOH solution. To this reaction mixture is added a solution of 0.86 g (3.77 mmol) 1-methyl-α-trichloromethyl-pyrrole-2-methanol in 3 ml methanol, and then the remaining KOH solution is added dropwise over 5 min. After 1.5 hours, the flask is cooled and the reaction is washed with 15 ml Et$_2$O. The aqueous phase is acidified with concentrated HCl to give pH 1–2, saturated with solid NaCl, and extracted three times with 30 ml of Et$_2$O. The latter organic extracts are combined and dried over Na$_2$SO$_4$. The solvent is removed under reduced pressure to afford 0.40 g (76%) of crude 1-methylpyrrole-2-acetic acid.

Homologs of this compound, wherein the methyl has been replaced by other lower alkyl groups having up to 6 carbons are prepared by analogous procedures. Thus, by following the procedure of Example II, but utilizing the 1-loweralkyl-α-trichloromethyl-pyrrole-2-methanol wherein the loweralkyl radical is the same as in the desired end product, there are prepared the compounds 1-ethylpyrrole-2-acetic acid, 1-propylpyrrole-2-acetic acid, 1-isobutylpyrrole-2-acetic acid, 1-butylpyrrole-2-acetic acid, 1-pentylpyrrole-2-acetic acid and 1-hexylpyrrole-2-acetic acid.

EXAMPLE III

Pyrrole-2-acetic acid

A solution of 16.4 g (0.0775 mol) of α-trichloromethylpyrrole-2-methanol in 20 ml of methylene chloride and a solution of 26.0 g of potassium hydroxide (0.46 mol) in 170 ml of water are added concurrently over 15 min. to a suspension of 53.9 g (0.31 mol) of sodium dithionite in 85 ml of water at 55° under nitrogen. The methylene chloride is distilled off. The mixture is stirred at 55° for 90 min. It is cooled, and the aqueous solution is washed with ether. The aqueous solution is acidified with hydrochloric acid and extracted four times with ether. The ether solution is dried ($MgSO_4$). The solvent is evaporated. There is obtained 6.6 g of semisolid, brown pyrrole-2-acetic acid. It is taken up in ether. A 3 ml sample of ethylamine is added. The precipitated ethylammonium salt is collected by filtration. It is recrystallized from 2-propanol to give 3.7 g (28% yield), m.p. 124°-5°(d). A 1.0 g sample of the salt is dissolved in $H_2O$, acidified with hydrochloric acid and extracted with ether five times. The ether solution is dried and the solvent is evaporated in vacuo. The residue is triturated with hexane and collected. There is obtained 0.84 g of pyrrole-2-acetic acid m.p. 83°-4°(d) [reported 83-4(d), C. Nenitzescu and E. Salomica, Ber; 64 1928 (1931)].

EXAMPLE IV

Methyl N-Methylpyrrole-2-acetate

Over a 15 minute period a solution of 34.6 g (0.525 mol) of potassium hydroxide pellets in 80 ml of $H_2O$ is dripped into a mechanically stirred suspension of 53.3 g (0.306 mol) of sodium hydrosulfite and 20.0 g (0.0875 mol) of N-methyl-α-trichloromethylpyrrole-2-methanol in 80 ml of $H_2O$ and 10 ml of methanol. An ice bath is used to maintain the internal temperature no higher than 62° C., and the reaction mixture is stirred with ice bath present for 15 minutes after the addition is complete. One hour later, the reaction mixture is acidified with concentrated hydrochloric acid to give pH 1-2, and the resulting suspension is extracted with three 250 ml portions of $Et_2O$. The combined organic phases are dried over $Na_2SO_4$, and then concentrated under reduced pressure to afford 10.05 g of orangebrown solid, crude N-methylpyrrole-2-acetic acid.

A 9.70 g sample of the above crude acid is dissolved in 45 ml of dimethylsulfoxide, and 9.62 g (0.0698 mol) of potassium carbonate is added. Over 5 minutes 4.3 ml (0.0698 mol) of iodomethane was added to the vigorously stirred suspension, and after two hours at room temperature, the reaction was poured into 350 ml of $H_2O$. The resulting suspension was extracted with four 100 ml portions of diethyl ether, and the combined organic phases were washed with 50 ml of $H_2O$, and 50 ml of brine, then dried over sodium sulfate. The solvent was removed under reduced pressure and the residue was distilled at 80°-90° C./1 mm, to afford 5.13 g of yellow liquid, methyl N-methylpyrrole-2-acetate. Gas chromatography revealed that the acid was 94.9% pure, for a 36.4% conversion of N-methyl-α-trichloromethyl-pyrrole-2-methanol to methyl N-methylpyrrole-2-acetate.

NMR: $\delta^{CDCl_3}$ 6.54 (m, 1H), 6.00 (m, 2H), 3.64 (S, 3H) 3.57 (S, 2H), and 3.51 (S, 3H).

EXAMPLE V

1,4-Dimethylpyrrole-2-acetic Acid

A mixture of 13.9 g (0.08 mol) of sodium dithionite in 20 ml of water and 5 ml of ethanol was heated to 55° C. under argon. A 4.8 g (0.02 mol) sample of 1,4-dimethyl-α-trichloromethylpyrrole-2-methanol was added in one portion. A solution of 6.7 g (0.12 mol) of KOH in 20 ml of water was added dropwise over 20 mins. The reaction was stirred for 70 more mins. at 55°. It was cooled and acidified with concentrated HCl. Sodium chloride was added. The mixture was extracted three times with ether. The ether solution was washed with brine, dried ($MgSO_4$) and evaporated to give 2.1 g (69%) yield of a yellow oil, primarily 1,4-dimethylpyrrole-2-acetic acid by TLC. Final purification was effected by chromatography on silica gel using a 50:50 mixture of hexane: 1,1,1-trichloroethane as eluant. Evaporation of the compound bearing fraction and recrystallization from ether, hexane afforded white crystals, mp 86°-87° C. (d). The mp was undepressed by admixture with authentic material.

IR$\gamma^{nujol}$ 2750, 2650, 2550, 1705 sh, 1700, 1380, 1240, 1185, 920, 790, 740 $cm^{-1}$. The infrared spectrum was identical to authentic material.

EXAMPLE VI

1,4-Dimethylpyrrole-2-acetic Acid

A reference sample of 1,4-dimethylpyrrole-2-acetic acid was prepared as follows: A 9.05 g sample of ethyl 1,4-dimethylpyrrole-2-acetate [J. R. Carson and S. Wong, J. Med. Chem., 16, 172 (1973)] was heated under reflux with 30 ml of 10% sodium hydroxide solution for one hour. The solution was acidified with dilute HCl and extracted with ether. The ether was washed with brine and dried ($MgSO_4$). The solvent was evaporated in vacuo and the residue was triturated with hexane and collected by filtration to give 6.8 g (89% yield) of 1,4-dimethylpyrrole-2-acetic acid as a pink crystalline solid, mp 86°-7° C. (d).

EXAMPLE VII

Ethyl 1,4-Dimethylpyrrole-2-acetate

A 5.48 ml (0.042 mol) sample of diethyl sulfate was added to a suspension of 6.12 g (0.040) of 1,4-dimethylpyrrole-2-acetic acid and 16.6 g (0.12 mol) of potassium carbonate in 50 ml of DMSO. The mixture was stirred for 6 hours at room temperature. It was poured into water and extracted with ether. The ether extract was washed with brine, dried ($MgSO_4$) and the solvent was evaporated in vacuo. The oily residue was distilled to give 6.0 g of ethyl 1,4-dimethylpyrrole-2-acetate, bp 68° at 0.005 Torr as a colorless oil.

EXAMPLE VIII

1,4-Dimethyl-α-trichloromethylpyrrole-2-methanol

A solution of 12.08 g (0.082 mol) of chloral in 25 ml of ether was added dropwise to a solution of 7.8 g (0.082 mol) of 1,3-dimethylpyrrole [B. E. Maryanoff, J. Org. Chem., 44 4410 (1979)] and 0.4 ml of glacial acetic acid in 40 ml of ether at 15° for 30 minutes under nitrogen. The temperature was allowed to rise to 25° C. after 4 hours. A 10 mg sample of trichloroacetic acid was added. The mixture was stirred at 25° C. for 2 days. It was washed with dilute aqueous ammonia and brine, dried ($Na_2SO_4$) and the solvent evaporated in vacuo.

The residue was chromatographed on a Waters Associates, Prep LC/System 500 using 15% ether in hexane as the eluant. The second compound bearing fraction was collected. The solvent was evaporated in vacuo and the residue recrystallized from hexane to give 7.3 g of pink crystalline 1,4-dimethyl-α-trichloro-methylpyrrole-2-methanol, mp 55°–57° C., 37% yield. $^1$H NMR (CDCl$_3$) δ 6.3 (2H,m), 5.1 (1H,d,J=6 Hz), 3.5 (3H,s), 2.0 (3H,s).

I claim:

1. The process for preparing N-H and N-loweralkyl-pyrrole-2-acetic acids of the formula:

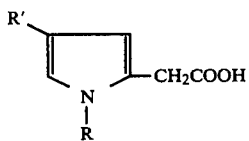

which comprises reacting a corresponding compound of the formula:

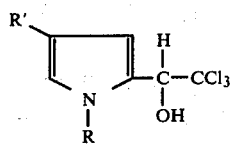

in the presence of sodium dithionite and of a base of the formula MOH, wherein in the foregoing formulas, R is hydrogen or loweralkyl, R' is hydrogen or loweralkyl and M is an alkali metal, an alkaline earth metal or a tetraalkylammonium.

2. The process of claim 1, wherein 1-methyl-α-trichloromethylpyrrole-2-methanol is reacted to make 1-methyl-pyrrole-2-acetic acid.

3. The process of claim 1, wherein α-trichloromethylpyrrole-2-methanol is reacted to make pyrrole-2-acetic acid.

4. The process of claim 1, wherein 1,4-dimethyl-α-trichloromethylpyrrole-2-methanol is reacted to make 1,4-dimethylpyrrole-2-acetic acid.

5. The process of claims 2, 3 or 4, wherein the reaction is conducted in the presence of an excess of both the sodium dithionite and the MOH base.

6. The process of claims 2, 3 or 4, wherein the MOH base is potassium hydroxide.

* * * * *